United States Patent
Hong et al.

(10) Patent No.: US 10,889,537 B2
(45) Date of Patent: Jan. 12, 2021

(54) METHOD FOR PRODUCING FLUORINE-CONTAINING DIALKYL CARBONATE COMPOUNDS

(71) Applicant: SAMHWA PAINTS INDUSTRIES CO., LTD., Ansan-si (KR)

(72) Inventors: Myeng Chan Hong, Pyeongtaek-si (KR); Yeong Sup Choi, Ansan-si (KR); Da Eun Kwon, Gunpo-si (KR); Jong Yun Kwak, Seoul (KR)

(73) Assignee: SAMHWA PAINTS INDUSTRIES CO., LTD., Ansan-si (KR)

( * ) Notice: Subject to any disclaimer, the term of this patent is extended or adjusted under 35 U.S.C. 154(b) by 76 days.

(21) Appl. No.: 16/336,703

(22) PCT Filed: Nov. 13, 2017

(86) PCT No.: PCT/KR2017/012791
§ 371 (c)(1),
(2) Date: Mar. 26, 2019

(87) PCT Pub. No.: WO2018/097529
PCT Pub. Date: May 31, 2018

(65) Prior Publication Data
US 2020/0231530 A1    Jul. 23, 2020

(30) Foreign Application Priority Data
Nov. 28, 2016  (KR) .................. 10-2016-0159015

(51) Int. Cl.
*C07C 68/02* (2006.01)
*C07C 68/08* (2006.01)

(52) U.S. Cl.
CPC .............. *C07C 68/02* (2013.01); *C07C 68/08* (2013.01)

(58) Field of Classification Search
CPC ................................ C07C 68/02; C07C 68/08
See application file for complete search history.

(56) References Cited

U.S. PATENT DOCUMENTS

| 5,659,062 A | 8/1997 | Yokoyama et al. |
| 2012/0141870 A1 | 6/2012 | Chen et al. |

FOREIGN PATENT DOCUMENTS

| JP | H0640951 A | 2/1994 |
| JP | H06219992 A | 8/1994 |
| KR | 100690010 B1 | 3/2007 |
| KR | 100744824 B1 | 8/2007 |
| WO | 2005/123656 A1 | 12/2005 |
| WO | 2014/050877 A1 | 4/2014 |

*Primary Examiner* — Rebecca L Anderson
(74) *Attorney, Agent, or Firm* — Nixon Peabody LLP; David S. Resnick; Nicole D. Kling

(57) ABSTRACT

The present invention relates to a method for producing fluorine-containing dialkyl carbonate compounds, which are suitable as non-aqueous solvents for non-aqueous electrolytes used in secondary batteries. When an alkyl chloroformate and an alcohol are reacted in the presence of an ether-containing imidazole derivative base, the reaction can be carried out at room temperature as compared with the prior art, and the products can be separated within a short time from the reactants. This is an economical process, and according to the present invention, it is possible to obtain alkyl carbonates containing fluorine atoms simply and without difficulty in the removal of solvents, salts formed during the reaction, and by-products.

6 Claims, No Drawings

METHOD FOR PRODUCING FLUORINE-CONTAINING DIALKYL CARBONATE COMPOUNDS

CROSS-REFERENCE TO RELATED APPLICATIONS

This application is a 35 U.S.C. § 371 National Phase Entry Application of International Application No. PCT/KR2017/012791 filed Nov. 13, 2017, which designates the U.S. and claims the benefit of foreign priority under 35 U.S.C. § 119(a) of Korean provisional application No. 10-2016-0159015 filed Nov. 28, 2016.

TECHNICAL FIELD

The present invention relates to a method for producing fluorine (F)-containing dialkyl carbonate compounds. More specifically, the present invention relates to a method for producing fluorine-containing dialkyl carbonate compounds by reacting an alkyl chloroformate and an alcohol in the presence of an ether-containing imidazole derivative base.

BACKGROUND ART

A lithium ion secondary battery is a non-aqueous electrolyte and are used by dissolving a lithium (Li) salt in a non-aqueous solvent such as ethylene carbonate, propylene carbonate, dimethyl carbonate or the like. Recent market demands for obtaining lithium ion batteries with higher energy density, higher power, and higher safety lead to the development of new solvents to improve the performance of batteries in electrolytes based only on carbonate. Currently used electrolytes are decomposed at 5V or more, and thus, the performance of the batteries is reduced, and further, safety problems may occur due to a low boiling point and high ignitability of the electrolytes. In order to solve these problems, research and production of linear carbonates containing fluorine atoms have actively proceeded.

As a method for synthesizing non-cyclic carbonates containing a fluorine atom, a method of carrying out the reaction by adding a sodium methoxide/methanol solution to a mixed solution of alcohol and a dimethyl carbonate and then heating the mixture at 100° C. for 6 hours is disclosed in Patent Document 1 (Mitsui Petrochemical Industries, Ltd. and Sony Corporation) issued in 1997 as a prior art 1. In this method, after completion of the reaction, an aqueous solution of ammonium chloride is added to the mixture to remove sodium methoxide, and the organic layer is washed with water and dried to obtain a product. However, there are disadvantages that sodium methoxide is highly reactive and thus dangerous, and it reacts violently upon contact with water and turns into sodium hydroxide.

In the method disclosed in Patent Document 2 (Du Pont de Nemours and Company) as a prior art 2, an alcohol and chloroformate are used as reactants, and pyridine is used as a base. The chloroformate is added dropwise by lowering a temperature to −10° C., and when the reaction is completed, 5% HCl is added and the mixture is extracted with ether. Then, the organic layer is washed with 5% NaHCO$_3$, and the product is isolated using a rotary evaporator.

In the method disclosed in Patent Document 3 (Daikin industries) as a prior art 3, an alcohol, methyl chloroformate, and diglyme as a solvent, are added, and when the temperature is lowered using ice bath, triethylamine is added dropwise while paying attention to heat generation. When the reaction is completed, the reaction mixture is washed with 1N HCl aqueous solution and the separated organic layer is purified using a 10-stage distillation purification tower to obtain a desired compound.

In Patent Document 4 as a prior art 4, chloroformate and an alcohol are reacted in the presence of 1-methylimidazole, and after completion of the reaction, the layers are separated. However, it is not easy to separate the formed 1-methylimidazole salt from the product, and the salt formed during the layer separation is highly viscous, and thus, a longer period of time is required for separation. In addition, when the formed salt is saturated with HCl, it is precipitated as solids, which may cause problems for industrialization.

PRIOR ART DOCUMENTS

Patent Documents (Patent Document 1) U.S. Pat. No. 5,659,062
(Patent Document 2) U.S. Patent Publication NO. 2012/0141870
(Patent Document 3) Korean Patent Publication No. 10-2015-0054951
(Patent Document 4) Korean Patent No. 10-0690010

DETAILED DESCRIPTION OF THE INVENTION

Technical Problem

In the above-mentioned prior arts 1 to 4, there are disadvantages that the separation and purification processes are complicated, the difference in the boiling point between the solvent and the product is small, it is difficult to perform separation, and a longer period of time is required to separate the layers due to viscosity. Further, there is a problem that the temperature should be lowered due to heat generation when a base is added dropwise.

In this regard, the present inventors have conducted extensive studies to solve the problems of the prior arts that the separation and purification processes are complicated, high stages of distillation column are required to separate the used solvent and the product, the salt is precipitated during layer separation, and a longer period of time is required to separate the product. As a result, the inventors have found that when an ether-containing imidazole derivative is used as a base and an alkyl chloroformate is reacted with an alcohol, not only the reaction can proceed at room temperature, but also the product can be easily and rapidly separated from the reaction mixture without the formation of solids. Accordingly, an object of the present invention is intended to improve the disadvantages encountered with conventional production methods, thus providing an economical and easy production method.

Technical Solution

The present invention relates to a method for producing a fluorine-containing dialkyl carbonate represented by the following Chemical Formula 3, including: reacting an alkyl chloroformate represented by the following Chemical Formula 1 and an alcohol represented by the following Chemical Formula 2 in the presence of an ether-containing imidazole derivative base:

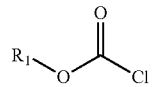

(Chemical Formula 1)

(Chemical Formula 2)

R²OH (Chemical Formula 3)

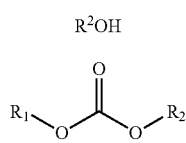

(wherein, $R_1$ and $R_2$ are each dependently an unsubstituted $C_1$-$C_{20}$ alkyl group and a fluorine-substituted $C_1$-$C_{20}$ alkyl group).

(Reaction Scheme 1)

$$R_1\diagdown_O\diagdown^{O}\diagdown_{Cl} + R_2OH \longrightarrow R_1\diagdown_O\diagdown^{O}\diagdown_O\diagdown^{R_2}$$

in Reaction Scheme 1, $R_1$ and $R_2$ are each independently as defined in Chemical Formulae 1, 2 and 3.

As a composition ratio, it is preferable to use 0.9 to 1.1 moles of the base, 0.9 to 1.1 moles of the alkyl chloroformate, and 0.9 to 1.1 moles of the alcohol. However, the mixing molar ratio is most suitably 1:1:1. By-product is HCl, and in order to remove these, base requires a molar ratio of 1. This is because the formed ionic liquid and product may be separated. If the base is used in a molar amount of more than 1, the product and the remaining base may be mixed. If the base is used in a molar amount of less than 1, the reaction is not completed.

The alkyl chloroformate may be reacted with the alcohol in the presence of the base at a temperature range of 0 to 70° C., and more preferably 10 to 35° C.

In addition, the separation of the product from the reactants may be achieved by layer separation. In this way, it is possible not only to avoid the use of sodium methoxide, which is difficult to handle, but also to separate the alcohol, which is difficult to be removed by a distillation method due to the formation of an azeotrope between the alcohol remaining after the reaction and the product. Thus, it is possible to easily separate the alcohol and the reactant by the layer separation due to the imidazole salt formed by the use of the imidazole base, and the separation process may be much more economical.

As the base, one or two selected from 1-(methoxymethyl) imidazole, 1-(ethoxymethyl)imidazole, 1-(propoxymethyl) imidazole, 1-(butoxymethyl)imidazole, 1-(2-methoxyethyl) imidazole, 1-(2-ethoxyethyl)imidazole, 1-(2-propoxyethyl) imidazole, 1-(2-butoxyethyl)imidazole, 1-(3-methoxypropyl)imidazole, and 1-(3-ethoxypropyl) imidazole may be used. Among them, 1-(2-ethoxyethyl) imidazole is most preferable, because it enables an easy and rapid layer separation and can be reusable. The reaction time may be less than 6 hours, preferably from 2 to 4 hours.

Advantageous Effects

In the present invention, when an alkyl chloroformate and an alcohol are reacted in the presence of an ether-containing imidazole derivative as a base, it has advantages in that the reaction can proceed at room temperature as compared with the prior art, and the product can be easily separated from the reactants. This is, the method for producing alkyl carbonates containing fluorine atoms according to the present invention is a very simple process involving a rapid layer separation so as to remove the solvents, the by-products formed during the reaction, and the formed salts without the formation of solids, and thus has an advantage of obtaining fluorine-containing linear alkyl carbonates. Accordingly, the production method of the present invention can be effectively applied to the production of fluorine-containing dialkyl carbonates used for various applications such as electrolytes of lithium ion secondary batteries, medicines and fine chemicals, pesticides, polar aprotic solvents, synthetic lubricating oils and the like.

DETAILED DESCRIPTION OF THE EMBODIMENTS

Hereinafter, the present invention will be described in more detail by way of Examples. It should be understood that the terms or words used in the specification and the appended claims should not be construed as limited to general and dictionary meanings, but interpreted based on the meanings and concepts corresponding to technical aspects of the present disclosure. Therefore, the embodiments disclosed in the present specification are merely the most preferred embodiments of the present disclosure, and not all of them represent the technical ideas of the present disclosure, and thus it should be understood that there may be various equivalents and modified examples that could substitute therefore at the time of filing the present application.

Example 1: Preparation of Methyl 2,2,2-trifluoroethyl Carbonate 100 g of methyl chloroformate and 106 g of 2,2,2-trifluoroethanol were added to a 1000-mL reactor equipped with a stirrer, and the mixture was stirred at room temperature for 30 minutes. 149 g of 1-(2-ethoxyethyl)imidazole was placed in a dropping funnel equipped in the reactor head, then added dropwise for 2 hours and stirred at room temperature for 3 hours. After completion of the reaction, the layers were separated to obtain methyl 2,2,2-trifluoroethyl carbonate as a transparent liquid in a yield of 88%.

Examples 2 to 4: Preparation of Methyl Fluoroalkyl Carbonate Compounds

The reaction was carried out in the same manner as in Example 1, except that the type of alcohols was varied. The results are shown in Table 1 below.

TABLE 1

| Examples | Alcohol compounds | Yield (%) |
|---|---|---|
| 2 | Hexafluoro-iso-propanol | 85 |
| 3 | 2,2,3,3-tetrafluoropropanol | 80 |
| 4 | 2,2,3,3,3-pentafluoropropanol | 90 |

Example 5: Preparation of Ethyl 2,2,2-trifluoroethyl Carbonate 100 g of ethyl chloroformate and 92 g of 2,2,2-trifluoroethanol were added to a 1000-mL reactor equipped with a stirrer, and the mixture was stirred at room temperature for 30 minutes. 129 g of 1-(2-ethoxyethyl)imidazole was placed in a dropping funnel equipped in the reactor head, then added dropwise for 2 hours and stirred at room temperature for 3 hours. After completion of the reaction, the layers were separated to obtain ethyl 2,2,2-trifluoroethyl carbonate as a transparent liquid in a yield of 92%.

Examples 6 to 8: Preparation of Ethyl Fluoroalkyl Carbonate

The reaction was carried out in the same manner as in Example 5, except that the type of alcohol compounds was varied. The results are shown in Table 2 below.

TABLE 2

| Examples | Alcohol compounds | Yield (%) |
|---|---|---|
| 6 | Hexafluoro-iso-propanol | 85 |
| 7 | 2,2,3,3-tetrafluoropropanol | 85 |
| 8 | 2,2,3,3,3-pentafluoropropanol | 90 |

Examples 9 to 14: Preparation of Fluorodialkyl Carbonate

The reaction was carried out in the same manner as in Example 1, except that the molar ratio was varied. The results are shown in Table 3 below.

TABLE 3

| Examples | Methyl chloroformate | 2,2,2-trifluoroethanol | 1-(2-ethoxyethyl) imidazole | Yield (%) |
|---|---|---|---|---|
| 9 | 0.9 | 1 | 1 | 65 |
| 10 | 1 | 0.9 | 1 | 72 |
| 11 | 1 | 1 | 0.9 | 70 |
| 12 | 1.1 | 1 | 1 | 88 |
| 13 | 1 | 1.1 | 1 | 88 |
| 14 | 1 | 1 | 1.1 | 60 |

Examples 15 to 19: Preparation of Fluorodialkyl Carbonate

The reaction was carried out in the same manner as in Example 1, except that the reaction temperature was varied. The results are shown in Table 4 below.

TABLE 4

| Examples | Reaction Temperature (° C.) | Yield (%) |
|---|---|---|
| 15 | 0 | 45 |
| 16 | 10 | 88 |
| 17 | 35 | 88 |
| 18 | 50 | 85 |
| 19 | 70 | 70 |

Examples 20 to 24: Preparation of Fluorodialkyl Carbonate

The reaction was carried out in the same manner as in Example 1, except that the reaction time was varied. The results are shown in Table 5 below.

TABLE 5

| Examples | Reaction Time (h) | Yield (%) |
|---|---|---|
| 20 | 0.5 | 50 |
| 21 | 1 | 60 |
| 22 | 2 | 80 |
| 23 | 4 | 88 |
| 24 | 6 | 88 |

The invention claimed is:

1. A method for producing a dialkyl carbonate represented by the following Chemical Formula 3, comprising:

reacting an alkyl chloroformate represented by the following Chemical Formula 1 and an alcohol represented by the following Chemical Formula 2 in the presence of a base, wherein the base is one or two or more selected from 1-(methoxymethyl)imidazole, 1-(ethoxymethyl)imidazole, 1-(propoxymethyl)imidazole, 1-(butoxymethyl)imidazole, 1-(2-methoxyethyl)imidazole, 1-(2-ethoxyethyl)imidazole, 1-(2-propoxyethyl)imidazole, 1-(2-butoxyethyl)imidazole, 1-(3-methoxypropyl)imidazole, and 1-(3-ethoxypropyl)imidazole:

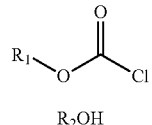

(Chemical Formula 1)

$R_2OH$ (Chemical Formula 2)

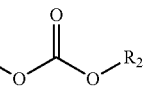

(Chemical Formula 3)

wherein, $R_1$ and $R_2$ are each independently an unsubstituted $C_1$-$C_{20}$ alkyl group and a fluorine-substituted $C_1$-$C_{20}$ alkyl group.

2. The method for producing a dialkyl carbonate of claim 1, wherein the reaction temperature is in the range of 10 to 35° C.

3. The method for producing a dialkyl carbonate of claim 1, wherein the reaction product is separated from the reactants by layer separation.

4. The method for producing a dialkyl carbonate of claim 1, wherein the base is 1-(2-ethoxyethyl)imidazole.

5. The method for producing a dialkyl carbonate of claim 1, wherein the reaction time is less than 6 hours.

6. The method for producing a dialkyl carbonate of claim 1, wherein the mixing molar ratio of the base, the alkyl chloroformate and the alcohol is 1:1:1.

* * * * *